United States Patent [19]

Patel

[11] 3,977,403

[45] Aug. 31, 1976

[54] CATHETER ADAPTER

[75] Inventor: Bhupendra C. Patel, Elgin, Ill.

[73] Assignee: The Kendall Company, Boston, Mass.

[22] Filed: Feb. 24, 1975

[21] Appl. No.: 552,028

[52] U.S. Cl. .............................. 128/221; 128/247; 251/149.1
[51] Int. Cl.² ........................................ A61M 5/00
[58] Field of Search ........... 128/221, 272, 247, 274, 128/216, 218 NV, 349 BV, DIG. 5; 251/149.1, 149.8

[56] References Cited
UNITED STATES PATENTS

| | | | |
|---|---|---|---|
| 1,180,665 | 4/1916 | McElroy | 128/218 NV |
| 3,659,587 | 5/1972 | Baldwin | 128/218 NV |
| 3,800,799 | 4/1974 | McWhorter | 128/247 X |
| 3,848,579 | 11/1974 | Villa-Real | 128/2 F |

FOREIGN PATENTS OR APPLICATIONS 1,078,650  11/1967  United Kingdom .......... 128/349 BV

*Primary Examiner*—John D. Yasko
*Attorney, Agent, or Firm*—Powell L. Sprunger

[57] ABSTRACT

An adapter for a syringe and a catheter comprising, a body member having first opening means to receive an end of the catheter, and means for sealingly engaging the catheter end. The body member has second opening means to receive a tip of the syringe, and means for sealingly engaging the syringe tip. Means is provided for establishing communication between the syringe tip and the one catheter end responsive to insertion of the tip into the second opening means and for closing the catheter end responsive to removal of the syringe tip from the second opening means.

16 Claims, 14 Drawing Figures

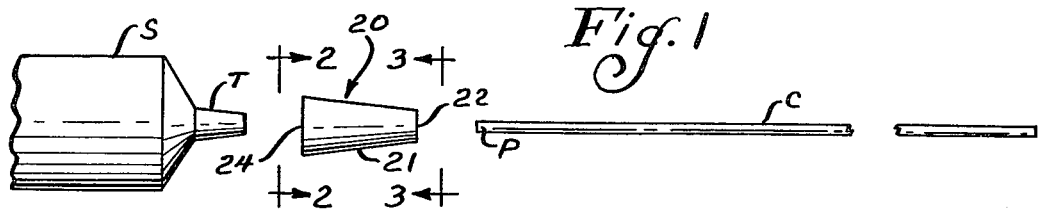
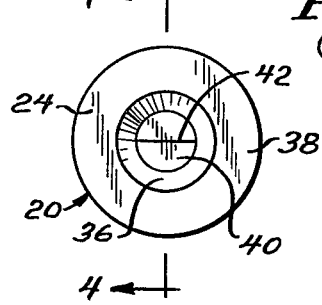
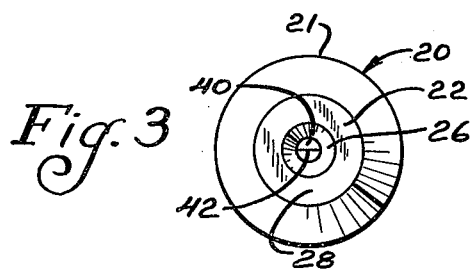
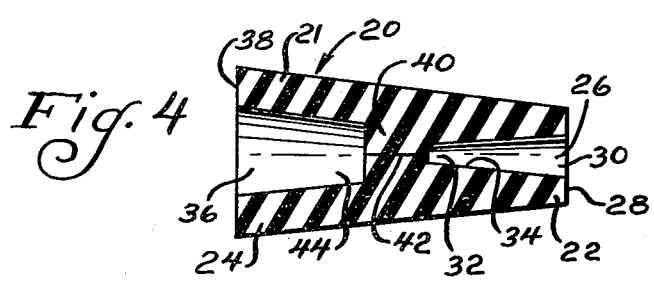
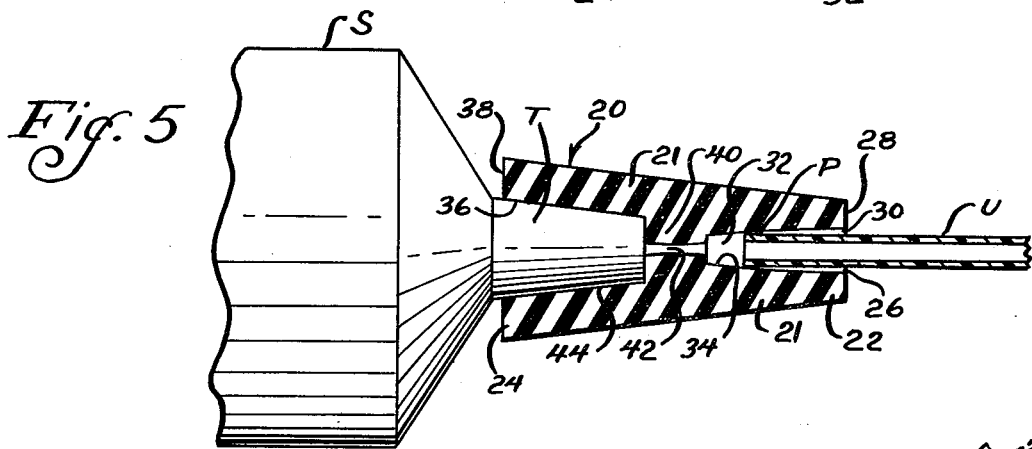
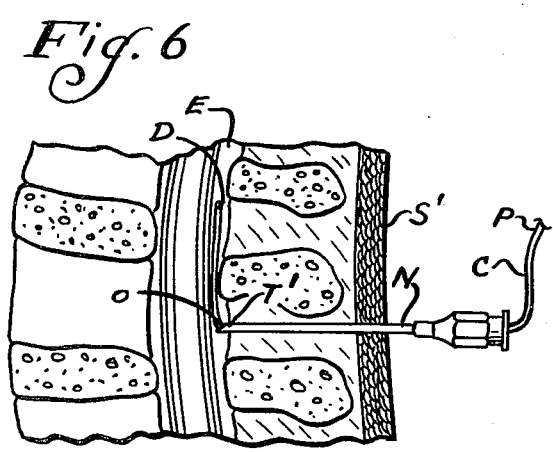
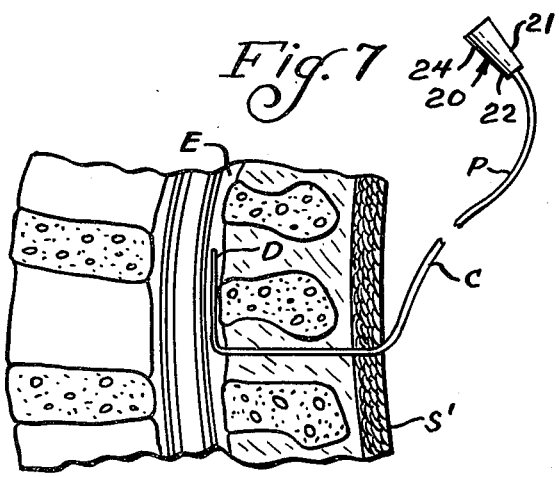

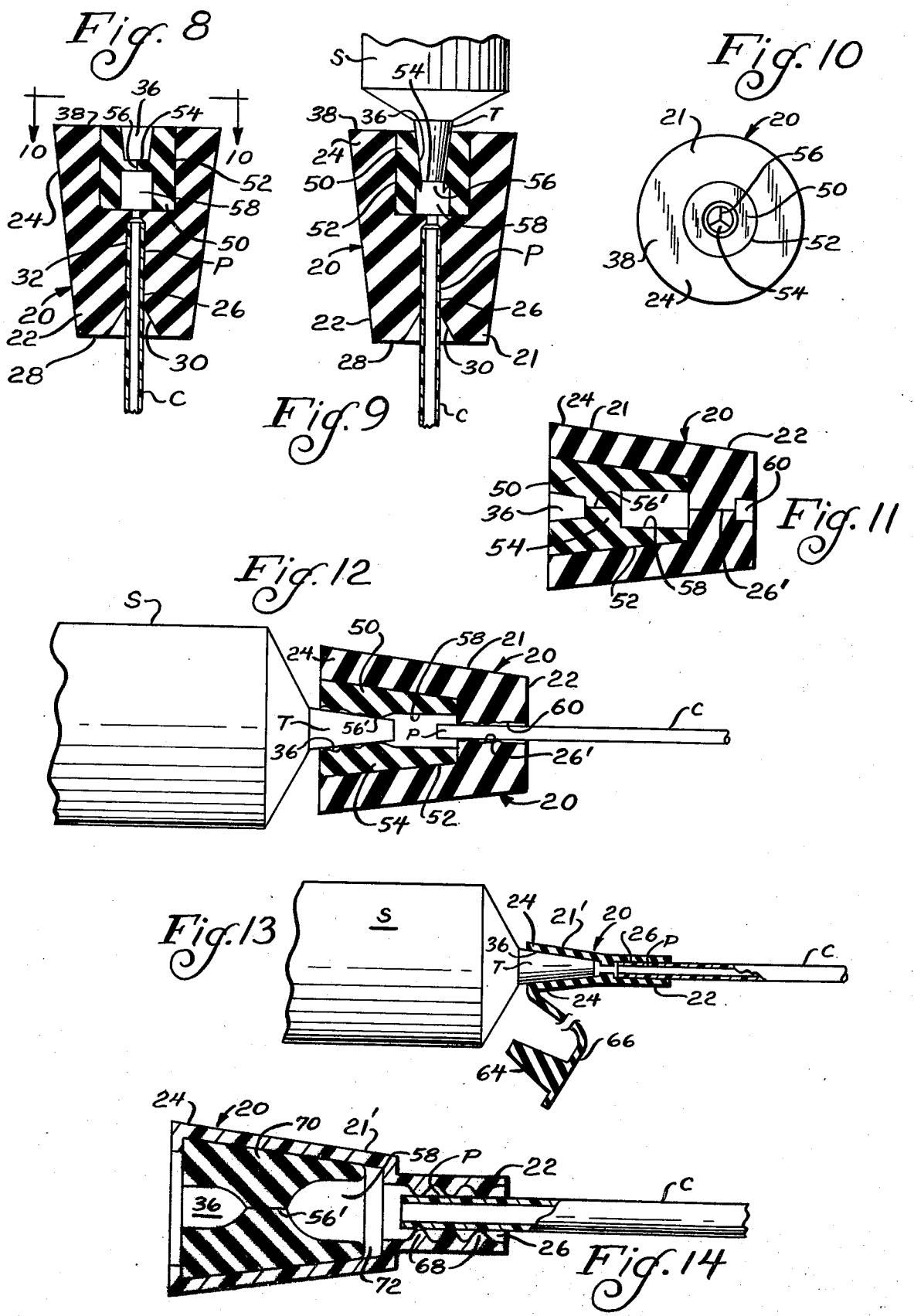

CATHETER ADAPTER

BACKGROUND OF THE INVENTION

The present invention relates to adapters.

During certain medical procedures, for example a continuous epidural or caudal spinal anesthesia procedure, it is necessary to connect a syringe to an end of a catheter. In a continuous epidural anesthesia procedure, a needle is positioned in a patient's body with an opening at one end of the needle positioned in the epidural space of the patient and with the other end of the needle extending outside the patient's body. A catheter of relatively small diameter is threaded through the needle and the needle opening until a distal end of the catheter is located in the epidural space, while a proximal end of the catheter extends outside the patient's body. The needle is removed from the patient's body and from the catheter to prevent obstruction if the operation takes place with the patient lying on his back and to prevent the needle from cutting the catheter during the operation. After removal of the needle, an anesthetic solution is injected through the catheter into the epidural space by a syringe which is connected to the proximal end of the catheter.

Accordingly, a connector or adapter must be provided for connecting the syringe to the proximal end of the catheter. The adapter should be positionable on the catheter after removal of the needle from the catheter, since the adapter would otherwise prevent removal of the needle from the catheter. It is also desirable that the adapter should permit easy placement on the catheter to expedite the procedure.

After the syringe has been connected to the adapter, the anesthetic solution is injected through the catheter into the epidural space. A relatively large amount of the solution is initially required for epidural anesthesia, with additional amounts of the solution being periodically injected during surgery. It is preferred that the syringe be removed from the adapter between injections, since if the syringe remains connected to the adapter and if the syringe inadvertently falls from the bed or other structure on which it is placed, the weight of the connected syringe may pull the catheter from the patient's body, necessitating repositioning of the catheter into the eqidural space during surgery if further anesthesia is required. It is desirable that the proximal end of the catheter be closed in a simple and expeditious manner to facilitate the anesthesia and surgical procedures, as well as prevent contamination to the inside of the adapter or catheter and possible contamination to the epidural space of the patient.

SUMMARY OF THE INVENTION

A principal feature of the present invention is to provision of an adapter of simplified construction which facilitates attachment to the tip of a syringe and a catheter.

The adapter of the present invention comprises, a body member having first opening means to receive an end of the catheter, and means for sealingly engaging the catheter end. The body member has second opening means to receive a tip of the syringe, and means for sealingly engaging the syringe tip. The body member also has means for establishing communication between the syringe tip and the catheter end responsive to insertion of the tip into the second opening means and for closing the catheter end responsive to removal of the syringe tip from the second opening means.

Thus, a feature of the present invention is that the catheter may be readily attached to the adapter by inserting the catheter end into the first opening means.

Another feature of the invention is that the syringe may be readily connected to the catheter by inserting the syringe tip into the second opening means.

A further feature of the invention is that the catheter end and syringe tip are automatically sealed by the sealing means when they are inserted into the respective opening means.

Another feature of the invention is that communication is automatically established between the catheter end and the syringe tip when the tip is inserted into the second opening means.

Yet another feature of the invention is that the syringe may be readily removed from the adapter by withdrawing the syringe tip from the second opening means.

Still another feature of the invention is that the catheter end is automatically closed by the adapter responsive to removal of the syringe tip from the second opening means.

Thus, a feature of the present invention is that the adapter prevents passage of air into the catheter when the syringe tip is removed from the adapter.

Another feature of the invention is that the adapter permits unimpeded passage of solution from the syringe to the catheter.

Another feature of the invention is that the adapter prevents contamination to the catheter and patient.

Further features will become more fully apparent in the following description of the embodiments of this invention and from the appended claims.

DESCRIPTION OF THE DRAWINGS

In the drawings:

FIG. 1 is a fragmentary elevational view of a syringe, a catheter, and an adapter of the present invention prior to attachment to the syringe and catheter;

FIG. 2 is an end view of the adapter taken as indicated along the line 2—2 of FIG. 1;

FIG. 3 is an end view of the adapter taken as indicated along the line 3—3 of FIG. 1;

FIG. 4 is a sectional view of the adapter taken substantially as indicated along the line 4—4 of FIG. 2;

FIG. 5 is a fragmentary sectional view of the syringe and catheter as connected to the adapter;

FIGS. 6 and 7 are diagrammatic views of a patient's body illustrating steps during placement of a catheter in the epidural space of the patient;

FIG. 8 is a sectional view of another embodiment of the adapter of the present invention;

FIG. 9 is a sectional view of the adapter of FIG. 8 showing the syringe and catheter connected to the adapter;

FIG. 10 is an end view of the adapter taken as indicated along the line 10—10 of FIG. 8;

FIG. 11 is a sectional view of another embodiment of the adapter of the present invention;

FIG. 12 is a sectional view of the adapter of FIG. 11 showing the syringe and catheter connected to the adapter;

FIG. 13 is a fragmentary elevational view, taken partly in section, illustrating another embodiment of the adapter of the present invention; and FIG. 14 is a fragmentary sectional view showing another embodiment of the adapter of the present invention.

DESCRIPTION OF THE PREFERRED EMBODIMENTS

Referring now to FIG. 1, there is shown a syringe S having a tip T, a catheter C, and an adapter generally designated 20 having a flexible body member 21, such as rubber. As will be described below, a proximal end P of the catheter C is connected to a first end 22 of the adapter 20, while the tip T of the syringe S is connected to a second end 24 of the adapter.

As shown in FIGS. 3 and 4, the first end 22 of the adapter 20 has a tapered channel or first opening means 26 extending from an end surface 28 of the first end 22. As shown in FIGS. 4 and 5, the channel 26 has an outer end 30 having a larger internal diameter than the outside diameter of the catheter, and an inner end 32 having an inside diameter smaller than the outside diameter of the catheter. Thus, as shown in FIG. 5, when the proximal end P of the catheter C is inserted through the enlarged outer end 30 of the channel 26, a wall 34 defining the channel 26 sealingly engages against the outer surface of the catheter at a location intermediate the outer and inner ends 30 and 32 of the channel 26. Accordingly, the catheter is readily attached to the adapter by inserting its proximal end into the channel 26 until sealing engagement with the wall 34 is made, thus preventing leakage between the wall 34 and the proximal end of the catheter. Additionally, the proximal end P of the catheter C is retained in the adapter by frictional engagement between the catheter and adapter wall 34.

As shown in FIGS. 2 and 4, the second end 24 of the adapter 20 has a tapered port or second opening means 36 extending from an outer surface 38 of the second adapter end 24. As illustrated in FIGS. 2-4, the adapter also has a wall portion 40 separating the port 36 and channel 26. The wall portion 40 has a slit 42 extending between the inner end 32 of the channel 26 and an inner end 44 of the port 36. As shown in FIGS. 2 and 3, the slit 42 preferably extends across the width of the inner end 32 of the channel 26. In this configuration of the adapter, the wall portion 40 and closed slit 42 prevent passage of air from the port 36 into the closed catheter end.

As illustrated in FIG. 5, when the tip T of the syringe S is inserted fully into the port 36, the syringe tip expands the second end 24 of the adapter 20, as well as the wall portion 40, and opens the slit 42. Thus, insertion of the syringe tip into the port 36 automatically opens the slit 42 and establishes communication between the syringe and the proximal end P of the catheter C, in order that anesthetic solution may be injected from the syringe through the opened slit 42 into the catheter C. When the syringe tip T is removed from the port 36 the second end 24 of the adapter 20 and the wall portion 40 contract, thus closing the slit 42 and preventing passage of fluid between the port 36 and the proximal end P of the catheter C. Accordingly, when the syringe tip is removed from the port 36, the closed slit prevents passage of air into the catheter, as well as back leakage of the solution immediately after the injection.

The use of the adapter of the present invention in connection with a continuous epidural spinal anesthesia procedure is described in connection with FIGS. 6 and 7 as follows, although it will be understood that the adapter may be utilized for other suitable purposes, such as in a continuous caudal spinal anesthesia procedure. As shown in FIG. 6, the tip T' of a Hustead needle N is inserted through the skin S' of the patient until an opening O in the needle tip T' is located in the epidural space E. Next, a catheter C is threaded through the needle N and opening O to position a distal end D of the catheter C in the epidural space E, as shown. The desired length of the catheter distal end D located in the epidural space may be determined by gradations spaced along the outer surface of the catheter C. In this configuration, the proximal end P of the catheter C extends outside the patient's body. The needle N is then removed from the patient's body and from the catheter C to prevent the needle from inadvertently cutting the catheter C during surgery.

As shown in FIG. 7, after the needle has been removed from the catheter, the proximal end P of the catheter C is inserted into the first opening means in the first end 22 of the adapter 20, as previously described, such that the proximal end p of the catheter C makes sealing engagement with the adapter 20. Next, the tip of the syringe is connected to the port in the second end 24 of the adapter 20, such that the slit in the adapter 20 opens to permit passage of the anesthetic solution from the syringe through the catheter C and into the epidural space E. When the desired amount of anesthetic solution has been injected into the epidural space, the syringe tip is removed from the adapter 20, to permit closure of the slit in the adapter and prevent passage of air through the slit and the catheter into the epidural space, which is at a negative pressure relative atmospheric pressure, as well as prevent back leakage of the solution immediately after the injection.

Accordingly, the adapter of the present invention permits easy placement of the adapter on the proximal end of the catheter. The syringe tip is also readily attached to the adapter, during which communication is automatically established between the syringe and the catheter. After the desired amount of solution has been injected into the epidural space, the syringe tip may be readily removed from the adapter, resulting in automatic closure of the catheter to the atmosphere.

Another embodiment of the adapter of the present invention is illustrated in FIGS. 8-10, in which like reference numerals designate like parts. As shown in FIG. 8, a first end 22 of the adapter 20 has an elongated channel 26 to receive and sealingly engage the proximal end P of the catheter C which is inserted into the channel 26, as previously described. The second end 24 of the adapter has a cavity 52, and a flexible insert 50 located in the cavity 52. The insert 50 has a port 36 to receive the tip of the syringe, and a wall 54 extending across an inner end of the port 36. The wall 54 has a plurality of slits 56, as best shown in FIG. 10, extending between the port 36 and a channel 58 which communicates with the proximal end P of the catheter C. As shown in FIGS. 8 and 10, the closed slits 56 prevent passage of air from the atmosphere or leakage through the wall 54 into the proximal end P of the catheter C.

As shown in FIG. 9, the tip T of the syringe S may be inserted through the wall 54 to open the slits 56 and establish communication between the syringe tip and the proximal end p of the catheter C. In this configuration, the inner wall of the insert 50 sealingly engages against the outer surface of the syringe tip T. Thus, the anesthetic solution may be injected from the syringe through the channel 58 into the proximal end P of the catheter C. After the desired amount of anesthetic solution has been injected into the catheter C, the syringe tip T is removed from the insert 50, during which the slits 56 in the wall 54 automatically close to prevent passage of air from the atmosphere into the channel 58 and the proximal end P of the catheter C or leakage from the catheter.

Another embodiment of the adapter 20 of the present invention is illustrated in FIGS. 11 and 12, in which like reference numerals designate like parts. In this embodiment, the first end 22 of the adapter 20 has an opening 60 adjacent its outer surface to direct the proximal end P of the catheter C into a slit 26' which extends between the opening 60 and a channel 58. The proximal end P of the catheter C is inserted through the slit 26' until the proximal end of the catheter is located in the channel 58. In this configuration, the adapter wall defining the slit 26' sealingly engages against the outer surface of the catheter C to prevent passage of fluid between the wall defining the slit and the outer surface of the catheter.

The insert 50 in the second end 24 of the adapter 20 has a port 36 to receive the tip T of the syringe S, and a wall 54 having a slit 56' extending between the port 36 and the channel 58. As shown in FIG. 12, the tip T of the syringe S is inserted through the slit 56' of the wall 54 until communication is established between the syringe tip T and the proximal end P of the catheter C, while the opened wall 54 sealingly engages against the tip of the syringe. After the desired amount of anesthetic solution has been injected from the syringe S into the catheter C, the syringe tip is removed from the slit 56' and the port 36, such that the slit 56' closes to prevent passage of air from the port 36 into the channel 58 and the proximal end P of the catheter C or leakage from the catheter.

Another embodiment of the present invention is illustrated in FIG. 13, in which like reference numberls designate like parts. In this embodiment, the adapter 20 has a body member 21' made of a relatively rigid material, such as plastic. The first end 22 of the adapter 20 has an elongated channel 26 to receive the proximal end P of the catheter C, with the wall of the first end 22 defining the channel 26 sealingly engaging against the outer surface of the catheter C. The second end 24 of the adapter 20 has a tapered port 36 to receive the tip T of the syringe S, such that the wall defining the port 36 sealingly engages against the tip T of the syringe S when the tip is fully inserted into the port 36. The anesthetic solution is injected from the syringe tip T into the proximal end P of the catheter C, as previously described. When the syringe tip T is removed from the port 36, a tapered plug 64 is inserted into the port 36 to close the port and prevent passage of air from the atmosphere into the catheter C or leakage from the catheter. For convenience, the plug 64 is connected to the body member 21' of the adapter 20 by a strap 66.

Another embodiment of the adapter 20 of the present invention is illustrated in FIG. 14, in which like reference numerals designate like parts. In this embodiment, the body member 21' is made of relatively rigid material, such as plastic. The first end 22 of the adapter has an elongated channel 26 to receive the proximal end P of the catheter C. The first end 22 of the adapter also has a plurality of internal sealing rings 68 to sealingly engage against the outer surface of the catheter C and prevent leakage of fluid around the outer surface of the catheter end P. The second end 24 of the adapter 20 has a cavity 72, and a flexible member 70 retained in the cavity 72. The flexible member 70 has a port 36 to receive the tip of the syringe, and has a slit 56' extending between the port 36 and a channel 58 which communicates with the proximal end P of the catheter C. When the tip of the syringe is inserted through the port 36 and the slit 56', the flexible member 70 sealingly engages the tip T, and communication is established between the syringe tip and the chamber 58, as well as the proximal end P of the catheter C. After the desired amount of anesthetic solution is injected by the syringe through the channel 58 and the catheter C, the syringe tip is removed from the slit 56' and the port 36, resulting in closure of the slot 56' to prevent passage of air into the channel 58 and the proximal end P of the catheter C.

The foregoing detailed description is given for clearness of understanding only, and no unnecessary limitations should be understood therefrom as modifications will be obvious to those skilled in the art.

I claim:
1. An adapter assembly, comprising:
   a syringe having a tip;
   a catheter; and
   a flexible body member having first opening means to receive an end of the catheter, means for sealingly engaging said catheter end, a port to receive and sealingly engage the syringe tip, and a wall portion separating the first opening means and said port, with said wall portion having normally closed slit means extending through the wall portion between the first openinng means and said port, said port having an internal size sufficiently less than the outer size of the syringe tip such that the syringe tip expands the body member and opens the slit means when the syringe tip is inserted into the port to establish communication between the syringe tip and the catheter, said body member contracting and the slit means closing responsive to removal of the syringe tip from the body member.

2. The adapter of claim 1 wherein the first opening means comprises a tapered channel extending into said body member, with an outer end of the channel having an internal diameter greater than the outside diameter of said catheter end, and with an inner end of the channel having an inner diameter less than the outside diameter of the catheter end, whereby a wall of the body member defining said channel sealingly engages against the outer surface of the catheter end.

3. The adapter of claim 1 wherein the first opening means includes a first portion having an internal diameter less than the outside diameter of said catheter end, whereby a wall of the body member defining said first portion sealingly engages the outer surface of the catheter end.

4. The adapter of claim 3 wherein the first opening means includes a second portion intermediate said first portion and the outer surface of the adapter having an internal diameter greater than the outer diameter of the one catheter end to receive the catheter end.

5. The adapter of claim 1 wherein said port is tapered.

6. The adapter of claim 1 wherein said slit means has a width at least approximately equal to the smallest internal diameter of the first opening means.

7. An adapter assembly, comprising:

a syringe having a tip;

a catheter having an outer surface and a lumen defining an inner surface; and a flexible body member having first opening means to receive an end of the catheter, means for sealingly engaging against and contacting only the outer surface of said catheter end, second opening means to receive a tip of the syringe, means for sealingly engaging the syringe tip, and means for establishing communication between the syringe tip and the one catheter end responsive to insertion of said tip into the second opening means and for closing the catheter end responsive to removal of the syringe tip from the second opening means.

8. The adapter of claim 7 including channel means connecting the first and second opening means.

9. The adapter of claim 7 wherein the body member includes a wall portion extending across the first opening means and having slit means to receive the catheter end, said slit means opening responsive to insertion of the catheter end into the slit means to establish communication between the tip and the catheter end, with the wall portion sealingly engaging against the outer surface of the catheter end to prevent passage of fluid around the catheter end.

10. An adapter assembly, comprising:

a syringe having a tip;

a catheter; and a flexible body member having first and second ends, said first end having a tapered channel extending from an outer surface of the body member, with the outer end of said channel having a greater internal diameter than the outer diameter of the catheter to receive an end of the catheter, and with the inner end of the channel having an internal diameter less than the outer diameter of said catheter end, whereby a wall of the first body member end defining said channel sealingly engages against the outer surface of the catheter end intermediate the inner and outer ends of the channel, said second body member end having a tapered port to receive the syringe tip with a wall of the second body member end defining the port sealingly engaging against the syringe tip, said body member having a wall separating said channel and port, said wall having a slit extending between the channel and port, said second body member end and wall expanding sufficiently responsive to insertion of the syringe tip into the port to establish communication between the syringe tip and catheter end and contracting responsive to removal of the syringe tip from the port to close the slit and prevent passage of fluid between the catheter end and said port.

11. The adapter of claim 10 wherein said slit has a width approximately equal to or greater than the internal diameter of the inner end of the channel.

12. An adapter assembly comprising, a syringe having a tip, a catheter, and a flexible body member having first and second ends, said first end having a channel to receive an end of the catheter with the body member sealingly engaging against the outer surface only of said catheter end, the second body member end having a port to receive the syringe tip with at least a portion of the port defining openable slit means, said slit means opening responsive to insertion of the syringe tip into the slit means and sealingly engaging against the syringe tip to establish communication between the tip and the catheter end and said slit means closing responsive to removal of the syringe tip from the slit means to prevent passage of fluid between the catheter end and the outside of the body member.

13. The catheter of claim 12 wherein said slit means comprises at least three slits extending through the wall portion and having one common end.

14. An adapter for a syringe tip and a catheter comprising, a relatively rigid body member having first and second ends, said first end having an elongated channel to receive an end of the catheter with a wall of the first body member end sealingly engaging against the outer surface of the catheter end, said second body member end having a tapered port to receive the syringe tip with a wall of the second body member end sealingly engaging against the syringe tip, said body member having a plug removably receivable in said port when the syringe tip is removed from the port, said plug closing the port to prevent passage of fluid between said catheter end and the outside of the body member, and a strap connecting the plug to the body member.

15. An adapter for a syringe tip and a catheter comprising, a relatively rigid body member having first and second ends, said first end having a channel to receive an end of the catheter, said second body member end having a chamber communicating with the channel and having a flexible sealing member retained in the chamber, said sealing member having slit means extending through the sealing member to receive and sealingly engage against the syringe tip, said slit means closing responsive to removal of the syringe tip from the sealing member to prevent passage of fluid between the outside of the body member and the one catheter end.

16. The adapter of claim 15 wherein the first body member end has a plurality of sealing rings in the channel for sealingly engaging against the outer surface of the catheter end.

* * * * *